US011058638B2

(12) United States Patent
Hoffman

(10) Patent No.: US 11,058,638 B2
(45) Date of Patent: Jul. 13, 2021

(54) TYROSINE DERIVATIVES AND COMPOSITIONS COMPRISING THEM

(71) Applicant: Tyme, Inc., Wilmington, DE (US)

(72) Inventor: Steven Hoffman, Mahwah, NJ (US)

(73) Assignee: Tyme, Inc., Wilmington, DE (US)

( * ) Notice: Subject to any disclaimer, the term of this patent is extended or adjusted under 35 U.S.C. 154(b) by 0 days.

(21) Appl. No.: 15/451,029

(22) Filed: Mar. 6, 2017

(65) Prior Publication Data

US 2017/0172924 A1 Jun. 22, 2017

Related U.S. Application Data

(62) Division of application No. 14/062,194, filed on Oct. 24, 2013, now Pat. No. 9,585,841.

(60) Provisional application No. 61/894,279, filed on Oct. 22, 2013.

(51) Int. Cl.

| | | |
|---|---|---|
| *A61K 9/14* | (2006.01) | |
| *A61N 5/02* | (2006.01) | |
| *A61K 31/198* | (2006.01) | |
| *A61K 47/18* | (2017.01) | |
| *A61N 5/06* | (2006.01) | |
| *A61N 5/10* | (2006.01) | |
| *A61K 38/00* | (2006.01) | |
| *A61K 45/06* | (2006.01) | |
| *A61K 33/40* | (2006.01) | |
| *A61K 45/00* | (2006.01) | |

(52) U.S. Cl.
CPC .............. *A61K 9/145* (2013.01); *A61K 9/141* (2013.01); *A61K 31/198* (2013.01); *A61K 33/40* (2013.01); *A61K 38/00* (2013.01); *A61K 45/00* (2013.01); *A61K 45/06* (2013.01); *A61K 47/183* (2013.01); *A61N 5/022* (2013.01); *A61N 5/062* (2013.01); *A61N 5/10* (2013.01); *A61N 2005/0659* (2013.01); *A61N 2005/0661* (2013.01); *A61N 2005/0662* (2013.01); *A61N 2005/1098* (2013.01)

(58) Field of Classification Search
None
See application file for complete search history.

(56) References Cited

U.S. PATENT DOCUMENTS

| | | | |
|---|---|---|---|
| 4,117,161 A | 9/1978 | Pozuelo | |
| 4,165,382 A | 8/1979 | Pozuelo | |
| 4,189,604 A | 2/1980 | Umezawa et al. | |
| 4,240,975 A | 12/1980 | Umezawa et al. | |
| 4,389,415 A | 6/1983 | Scriabine | |
| 4,806,360 A | 2/1989 | Leong et al. | |
| 5,073,541 A | 12/1991 | Taylor et al. | |
| 5,206,018 A | 4/1993 | Sehgal et al. | |
| 5,225,435 A | 7/1993 | Pawelek et al. | |
| 5,310,539 A | 5/1994 | Williams | |
| 5,576,290 A | 11/1996 | Hadley | |
| 5,674,839 A | 10/1997 | Hruby et al. | |
| 5,683,981 A | 11/1997 | Hadley et al. | |
| 5,714,576 A | 2/1998 | Hruby et al. | |
| 6,359,001 B1 | 3/2002 | Drago | |
| 7,452,868 B2 | 11/2008 | Kuzma et al. | |
| 7,482,018 B2* | 1/2009 | Soane .................. | A61K 9/1075 424/400 |
| 2002/0044968 A1* | 4/2002 | van Lengerich ........ | B29B 7/482 424/469 |
| 2002/0128304 A1 | 9/2002 | D'Amato | |
| 2003/0059471 A1 | 3/2003 | Compton et al. | |
| 2003/0232767 A1 | 12/2003 | Agrawal | |
| 2005/0165301 A1 | 7/2005 | Smith et al. | |
| 2006/0002852 A1* | 1/2006 | Saltzman ............. | A61K 9/0019 424/1.11 |
| 2006/0063699 A1 | 3/2006 | Larsen | |
| 2006/0240092 A1* | 10/2006 | Breitenkamp ....... | A61K 9/1075 424/450 |
| 2007/0248537 A1* | 10/2007 | Yang .................. | A61K 51/0491 424/1.49 |
| 2009/0030067 A1 | 1/2009 | Wosikowski-Buters | |
| 2009/0142337 A1 | 6/2009 | Squires | |
| 2010/0104660 A1 | 4/2010 | Yu | |
| 2010/0216781 A1 | 8/2010 | Perrin-Ninkovic | |

(Continued)

FOREIGN PATENT DOCUMENTS

| | | | |
|---|---|---|---|
| CN | 101516899 A | 8/2009 | |
| CN | 102088960 A | 6/2011 | |
| CN | 104220057 A | 12/2014 | |

(Continued)

OTHER PUBLICATIONS

Perry, "Surgical Management of Pheochromocytoma with the Use of Metyrosine", Ann. Surg., pp. 621-628, Nov. 1990 (Year: 1990).*
Böni et al., "Radioiodine-labelled alpha-methyl-tyrosine in malignant melanoma: cell culture studies and results in patients", British Journal of Dermatology, Jul. 1997, vol. 137, Issue 1, 96-100.
Brogden, "alpha-Methyl-p-tyrosine: a review of its pharmacology and clinical use", Drugs, Feb. 1981, 21(2), 81-89.
Cabrera López et al., "Effects of rapamycin on angiomyolipomas in patients with tuberous sclerosis", Nefrologia, Apr. 2011, 31(3), 292-298.

(Continued)

*Primary Examiner* — Robert T. Crow
*Assistant Examiner* — John P Nguyen
(74) *Attorney, Agent, or Firm* — BakerHostetler

(57) ABSTRACT

Provided herein are methods comprising providing a tyrosine derivative and a solid particulate material (and, optionally, melanin) and applying force to said tyrosine derivative and said solid particulate material for a time and under conditions effective to impregnate at least one of said tyrosine derivative and said solid particulate material with the other of said tyrosine derivative and said solid particulate material. The invention also provides compositions comprising at least one of a tyrosine derivative impregnated with a solid particulate material and a solid particulate material impregnated with a tyrosine derivative.

13 Claims, No Drawings

(56) References Cited

U.S. PATENT DOCUMENTS

2013/0129840 A1* 5/2013 Sheshbaradaran ..... A61K 31/31 424/649

FOREIGN PATENT DOCUMENTS

| JP | 64-2554 | 1/1989 |
|---|---|---|
| JP | 2-286602 A | 11/1990 |
| JP | 2010534226 A | 11/2010 |
| JP | 2011516443 A | 5/2011 |
| WO | WO 1994/10968 | 5/1994 |
| WO | WO 2002/100885 | 12/2002 |
| WO | WO 2005/072061 | 8/2005 |
| WO | 2007120153 A1 | 10/2007 |
| WO | WO 2009/054001 | 4/2009 |
| WO | WO 2009/109649 | 9/2009 |
| WO | WO 2009/131631 | 10/2009 |
| WO | WO 2010/022243 | 2/2010 |
| WO | WO 2010/118419 | 10/2010 |
| WO | WO 2011/112576 | 9/2011 |
| WO | WO 2013/109610 | 7/2013 |
| WO | 2015061288 A1 | 4/2015 |
| WO | WO-2015/061256 | 4/2015 |

OTHER PUBLICATIONS

Chembase.cn, http://en.chembase.cn/substance-34924.html, retrieved Feb. 7, 2014.
Chemwatch, "A-Methyl-DL-Tyrosine", Material Safety Data Sheet, Mar. 11, 2011, pp. 1-7.
Chen, "Progress in the development of bestatin analogues as aminopeptidases inhibitors", Current Medical Chemistry, Mar. 2011, vol. 18, No. 7, 964-976.
Chhun et al., "7. The Cytochrome P-450 2C9/2C19 but Not the ABCB1 Genetic Polymorphism May Be Associated With the Liver Cytochrome 3A4 Induction by Phenytoin", Journal of Clinical Psychopharmacology, Jun. 2012, vol. 32, No. 3, 429-431.
Chiu et al., "Lipid-Based Nanoparticulate Systems for the Delivery of Anti-Cancer Drug Cocktails: Implications on Pharmacokinetics and Drug Toxicities", Current Drug Metabolism, 2009, 10, 861-874.
Dorr et al., "Evaluation of melanotan-II, a superpotent cyclic melanotropic peptide in a pilot phase-I clinical study", Life Sciences, Apr. 1996, vol. 58, Issue 20, 1777-1784.
Ell, "Brain tumor uptake of iodo-alpha-methyl-tyrosine", Journal of Nuclear Medicine, Nov. 1991, 32(11), 2193-2194.
Espeillac et al., "S6 kinase 1 is required for rapamycin-sensitive liver proliferation after mouse hepatectomy", The Journal of Clinical Investigation, Jul. 2011, 121(7), 2821-2832.
Fan et al., "Impact of system L amino acid transporter 1 (LAT1) on proliferation of human ovarian cancer cells: a possible target for combination therapy with anti-proliferative aminopeptidase inhibitors", Biochemical Pharmacology, Sep. 15, 2010, vol. 80, Issue 6, 811-818.
Fitzgerald et al., "Effect of MELANOTAN, [Nle(4), D-Phe(7)]-alpha-MSH, on melanin synthesis in humans with MC1R variant alleles", Peptides, Feb. 2006, vol. 27, Issue 2, 388-394.
Ichimura et al., "Immunohistochemical expression of aminopeptidase N (CD13) in human lung squamous cell carcinomas, with special reference to Bestatin adjuvant therapy", Pathology International, Jun. 2006, vol. 56, Issue 6, 296-300.
International Patent Application No. PCT/US2014/061527: Notification Concerning Transmittal of International Preliminary Report on Patentability dated May 6, 2016, 5 pages.

Kargiotis et al., "Epilepsy in the cancer patient", Cancer Chemotherapy and Pharmacology, Mar. 2011, vol. 67, No. 3, 489-501.
Krige et al., "CHR-2797: An antiproliferative aminopeptidase inhibitor that leads to amino acid deprivation in human leukemic cells", Cancer Research, Aug. 15, 2008, 68(16), 6669-6679.
Kulke et al., "Future directions in the treatment of neuroendocrine tumors: consensus report of the National Cancer Institute Neuroendocrine Tumor clinical trials planning meeting", Journal of Clinical Oncology, Mar. 2011, vol. 29, No. 7, 934-943.
Landmark, "Antiepileptic Drugs in Non-Epilepsy Disorders—Relations between Mechanisms of Action and Clinical Efficacy", CNS Drugs, 2008, 22, 1, 27-47.
Liu et al., "Combinatorial effects of lapatinib and rapamycin in triple-negative breast cancer cells", Molecular Cancer Therapeutics, Aug. 2011, 10, 1460-1469.
Longo et al., "Efficacy and tolerability of long-acting octreotide in the treatment of thymic tumors: results of a pilot trial", American Journal of Clinical Oncology, Apr. 2012, 35(2), 105-109.
Nakagami, "A case of malignant pheochromocytoma treated with 131I-metaiodobenzylguanidine and alpha-methyl-p-tyrosine", Japanese Journal of Medicine, May-Jun. 1990, vol. 29, No. 3, 329-333.
Ram et al., "Failure of alpha-methyltyrosine to prevent hypertensive crisis in pheochromocytoma", Archives of Internal Medicine, Nov. 1985, vol. 145, No. 11, 2114-2115.
Ryakhovsky et al., "The first preparative solution phase synthesis of melanotan II", Beilstein Journal of Organic Chemistry, 2008, 4, 1-6.
Steinsapir et al., "Metyrosine and pheochromocytoma", Archives of Internal Medicine, Apr. 1997, vol. 157, No. 8, 901-906.
Tada, "Three cases of malignant pheochromocytoma treated with cyclophosphamide, vincristine, and dacarbazine combination chemotherapy and alpha-methyl-p-tyrosine to control hypercatecholaminemia", Hormone Research, Jan. 1998, vol. 49, No. 6, 295-297.
Taveria-DaSilva, "Sirolimus therapy in patients with lymphangioleiomyomatosis", Summaries for patients, Annals of Internal Medicine, Jun. 21, 2011, 154(12), 144.
Terauchi et al., "Inhibition of APN/CD 13 leads to suppressed progressive potential in ovarian carcinoma cells", BMC Cancer, 2007, 7, 1-12.
Tsukamoto et al., "Aminopeptidase N (APN)/CD13 inhibitor, Ubenimex, enhances radiation sensitivity in human cervical cancer", BMC Cancer, Mar. 2008, 8:74, 8 pages.
Voorhess, "Effect of alpha-methyl-p-tyrosine on 3,4-dihydroxyphenylalanine (DOPA) excretion of hamsters with melanotic melanoma", Cancer Research, Mar. 1968, 28, 452-454.
Zimmermann et al., "Prolonged Inhibition of Presynaptic Catecholamine Synthesis With α-Methyl-Para-Tyrosine Attenuates the Circadian Rhythm of Human TSH Secretion" J. Soc. Gynecol Investing, May/Jun. 2001, vol. 8 No. 3, 174-178.
5,5-Diphenylhydantoin, Chemical Book, [Online], [retrieved on Jun. 22, 2018], retrieved from the internet, <URL: http://www.chemicalbook.com/ChemicalProductProperty_JP_CB3139264.htm>.
Sustained somatostatin analog preparation—50ug OCTREOTIDE for s.c. injection "ASKA" package insert, [Online], ASKA Pharmaceutical Co., Ltd., 2016, [retrieved on Jun. 22, 2018] retrieved from the internet, <URL: http://database.japic.or.jp/pdf/newPINS/00066168.pdf>.
Sokol et al., "Preclinical animal data of the SM88 tyrosine isomer" Annals of Oncology, vol. 27, Supplement 6, XP055449216, Oct. 1, 2016.
International Preliminary Report on Patentability and Written Opinion issued in PCT/US2017/063865, dated Jun. 13, 2019.

* cited by examiner

TYROSINE DERIVATIVES AND COMPOSITIONS COMPRISING THEM

CROSS-REFERENCE TO RELATED APPLICATIONS

This application is a divisional of U.S. application Ser. No. 14/062,194, filed Oct. 24, 2013, which claims the benefit of U.S. Provisional Application No. 61/894,279, filed Oct. 22, 2013, the entireties of which are incorporated herein by reference.

TECHNICAL FIELD

The present inventions relate generally to compositions and methods for delivering pharmaceuticals.

BACKGROUND

To achieve an optimal therapeutic effect in humans or animals, various methods and processes have been developed to administer pharmaceutical compounds. A number of routes of administration have been developed for drug delivery including nasal, oral, intramuscular, intravenous, anal, and vaginal. These routes have shown varying degrees of success for different types of pharmaceuticals.

It is generally very expensive to develop new drug molecules and then bring them to market. There also have been numerous older drugs that initially showed promise but proved to be too toxic and/or unstable to use as medications. The use of alternative delivery techniques holds the potential to increase safety and/or efficacy for these and other drugs. The costs associated with developing such techniques are generally much lower than those associated with identifying and developing a completely novel drug.

There remains a need for drug delivery techniques having relatively broad applicability.

SUMMARY

The present invention provides compositions and methods for delivering solid particulate materials, particularly solid particulate materials comprising one or more pharmaceutically active ingredient such as those associated with the treatment of cancer. In certain embodiments, the invention provides methods comprising providing a tyrosine derivative and a solid particulate material (and, optionally, melanin) and applying force to said tyrosine derivative and said solid particulate material for a time and under conditions effective to impregnate at least one of said tyrosine derivative and said solid particulate material with the other of said tyrosine derivative and said solid particulate material. In other embodiments, the invention provides compositions comprising at least one of a tyrosine derivative impregnated with a solid particulate material and a solid particulate material impregnated with a tyrosine derivative. Such composition optionally can also include melanin. According to the present invention, such compositions are administered to a patient in need thereof. In other embodiments, the invention provides compositions comprising a tyrosine derivative, melanin, and a solid particulate material.

DETAILED DESCRIPTION OF ILLUSTRATIVE EMBODIMENTS

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment incudes from the one particular and/or to the other particular value. Similarly, when values are expressed as approximations, by use of the antecedent "about," it is understood that the particular value forms another embodiment. All ranges are inclusive and combinable.

As used herein, the terms "component," "composition," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

As used herein, the terms "treatment" or "therapy" (as well as different forms thereof) include preventative (e.g., prophylactic), curative or palliative treatment. As used herein, the term "treating" includes alleviating or reducing at least one adverse or negative effect or symptom of a condition, disease or disorder. This condition, disease or disorder can be cancer.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with respect to the particular compound, component or composition selected, the route of administration, and the ability of the components to elicit a desired result in the individual, but also with respect to factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage being at the discretion of the attending physician. Dosage regimes may be adjusted to provide improved therapeutic response. An effective amount is also one in which any toxic or detrimental effects of the components are outweighed by the therapeutically beneficial effects.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein can be prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein that contain, for example, both amino and carboxy groups, also include reference to their corresponding zwitterions.

The term "stereoisomers" refers to compounds that have identical chemical constitution, but differ as regards the arrangement of the atoms or groups in space. The term "enantiomers" refers to stereoisomers that are mirror images of each other that are non-superimposable.

The term "administering" means either directly administering a compound or composition of the present invention, or administering a prodrug, derivative or analog which will form an equivalent amount of the active compound or substance within the body.

The terms "subject," "individual," and "patient" are used interchangeably herein, and refer to an animal, for example a human, to whom treatment, including prophylactic treatment, with the pharmaceutical composition according to the present invention, is provided. The term "subject" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys.

The term "inhibitor" as used herein includes compounds that inhibit the expression or activity of a protein, polypeptide or enzyme and does not necessarily mean complete inhibition of expression and/or activity. Rather, the inhibition includes inhibition of the expression and/or activity of a protein, polypeptide or enzyme to an extent, and for a time, sufficient to produce the desired effect.

The term "promoter" as used herein includes compounds that promote the expression or activity of a protein, polypeptide or enzyme and does not necessarily mean complete promotion of expression and/or activity. Rather, the promotion includes promotion of the expression and/or activity of a protein, polypeptide or enzyme to an extent, and for a time, sufficient to produce the desired effect.

Representative therapeutic treatment methods include those in which the cancer is non-small cell lung cancer, ovarian cancer, breast cancer, cervical cancer, pancreatic cancer, stomach cancer, brain cancer, spinal cancer, liver cancer, bone cancer, osteosarcoma, lymphoid cancer, thyroid cancer, prostate cancer, breast cancer, ovarian cancer, cervical cancer, or testicular cancer. In other embodiments, the cancer is leukemia or lymphoma.

In certain embodiments, the invention provides methods comprising providing a tyrosine derivative and a solid particulate material and applying force to said tyrosine derivative and said solid particulate material for a time and under conditions effective to impregnate at least one of said tyrosine derivative and said solid particulate material with the other of said tyrosine derivative and said solid particulate material. In other embodiments, the invention provides a composition comprising at least one of a tyrosine derivative impregnated with a solid particulate material and a solid particulate material impregnated with a tyrosine derivative. In other embodiments, the invention provides methods comprising providing a tyrosine derivative, melanin, and a solid particulate material; applying force to said tyrosine derivative, said melanin, and said solid particulate material for a time; and administering said tyrosine derivative, melanin, and said solid particulate material to a patient in need thereof.

The tyrosine derivative can be capable of existing in isomeric forms. Specifically, the tyrosine derivative can be in its L-form or in its D-form.

Representative tyrosine derivatives include one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-Tyr(TBU)-allyl ester HCl, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl)methoxy]phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl)oxy]benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyr-OME HCl, H-3,5-diiodo-tyr-OME HCl, H-D-3,5-diiodo-tyr-OME HCl, H-D-tyr-OME HCl, D-tyrosine methyl ester hydrochloride, D-tyrosine-ome HCl, methyl D-tyrosinate hydrochloride, H-D-tyr-OMe HCl, D-tyrosine methyl ester HCl, H-D-Tyr-OMe-HCl, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr (3,5-I2)-OSu, Fmoc-tyr(3-NO2)-OH, α-methyl-L-tyrosine, α-methyl-D-tyrosine, and α-methyl-DL-tyrosine. In certain embodiments of the invention, the tyrosine derivative is α-methyl-L-tyrosine. In other embodiments the tyrosine derivative is α-methyl-D-tyrosine.

In suitable embodiments of the invention, the solid particulate material is soluble in water. In other suitable embodiments of the invention, the solid particulate material is not soluble in water.

In other embodiments of the invention, the solid particulate material is or comprises a pharmaceutically active ingredient. That pharmaceutically active ingredient can have therapeutic activity in the treatment of cancer. A representative solid particulate material is or comprises at least one of a selective estrogen receptor modulator, an aromatase inhibitor, a signal transduction inhibitor, a drug that modifies the function of proteins that regulate gene expression and other cellular functions, a drug that induces cancer cells to undergo apoptosis, and a drug that interferes with angiogenesis. Specifically, the pharmaceutically active ingredient is one or more of FDA-approved cancer drugs that include selective estrogen receptor modulators such as tamoxifen, toremifene (Fareston®), and fulvestrant (Faslodex®); aromatase inhibitors such as anastrozole (Arimidex®), exemestane (Aromasin®), and letrozole (Femara®); signal transduction inhibitors such as imatinib mesylate (Gleevec®), dasatinib (Sprycel®), nilotinib (Tasigna®), bosutinib (Bosulif®), lapatinib (Tykerb®), gefitinib (Iressa®), erlotinib (Tarceva®), temsirolimus (Torisel®), everolimus (Afinitor®), vandetanib (Caprelsa®), vemurafenib (Zelboraf®), and crizotinib (Xalkori®); drugs that modify the function of proteins that regulate gene expression and other cellular functions, such as vorinostat (Zolinza®), romidepsin (Istodax®), bexarotene (Targretin®), alitretinoin (Panretin®), tretinoin (Vesanoid®); drugs that induce cancer cells to undergo apoptosis, such as bortezomib (Velcade®), carfilzomib (Kyprolis™), and pralatrexate (Folotyn®); and drugs that interfere with angiogenesis, such as sorafenib (Nexavar®), sunitinib (Sutent®), pazopanib (Votrient®), regorafenib (Stivarga®), and cabozantinib (Cometriq™). Additional cancer drugs amenable to the present invention include denileukin diftitox (Ontak®), ziv-aflibercept (Zaltrap®), cisplatin, cisplatinum, (cis-diamminedichloroplatinum(II)), carboplatin, oxaliplatin, benzyl isothiocyanate, acetylcholine, and dihydrotestosterone (DHT). It should be appreciated, however, that other drugs that exist in particulate form may be amenable to processing in accordance with the present invention.

In another embodiment of the invention, the methods comprise providing a tyrosine derivative and a solid particulate material, applying force to said tyrosine derivative and said solid particulate material for a time and under conditions effective to achieve said impregnation, and adding hydrogen peroxide to said tyrosine derivative and said solid particulate material before or (preferably) after applying said force.

The forces applied to the tyrosine derivative and the solid particulate material (and, optionally, the melanin) need not be applied by any particular means. In certain embodiments of the invention, the force is applied by contacting said tyrosine derivative and said particulate material with at least one ceramic member, such as with a mortar and pestle. Preferred methods and devices, in which the force applied is accelerative force, are disclosed in the patent application entitled "High-Speed Centrifugal Mixing Devices and Methods of Use," filed on Oct. 22, 2013 and given U.S. patent application Ser. No. 14/059,837. When force is applied, the softer of the substances typically will be impregnated by the other(s). It should be appreciated, however, that the potential exists for the softer of two particulates to effect impregnation. In this regard, impregnation according to the present invention can involve, but does not require, a portion of one type of particulate extending into a portion of another type of particulate. For example, one type of particulate can be impregnated by another by fully surrounding or partially surrounding it. Thus, impregnation according to the present invention is effected where at least two different type of particulates are sufficiently conjoined that they exhibit the physical properties of a single type of particulate when exposed to normal material handling procedures such as sieving and pouring.

The compositions prepared in accordance with the present invention preferably are administered to a patient in need thereof. Representative routes of administration include oral, nasal, subcutaneous, intravenous, intramuscular, transdermal, vaginal, rectal or in any combination thereof. Nasal routes of administration can be especially useful because the blood brain barrier is thinnest in the posterior portion of the nasal cavity. This can be a preferred route of administration for treatments for, for example, brain and spinal cancers. The pharmaceutically active ingredient preferably is administered using the same dosages and dosing schedule that is otherwise applicable for a given indication, although it is believed that administration with a tyrosine derivative in accordance with the present invention will permit the use of a lower dosage to achieve the same efficacy.

In certain embodiments of the invention, the step of administering said tyrosine derivative and said solid particulate material (and, optionally, melanin) to a patient in need thereof can include applying an electromagnetic field to said patient. The electromagnetic field can be from radio waves, microwaves, infrared light, visible light, ultraviolet light, x-rays or gamma rays. While not intending to be bound by any particular mechanism of operation, it is believed that the application of the electromagnetic field can be used to increase the efficacy of one or more pharmaceutically active ingredient as, for example, by causing it and/or an accompanying molecule to enter a gaseous phase.

It will be appreciated by those skilled in the art that various modifications and alterations of the invention can be made without departing from the broad scope of the appended claims. Some of these have been discussed above and others will be apparent to those skilled in the art.

What is claimed:

1. A composition comprising at least one of a tyrosine derivative impregnated with a solid particulate material and a solid particulate material impregnated with a tyrosine derivative such that at least a portion of one type of particulate extends into a portion of a second type of particulate, wherein:

the tyrosine derivative is one or more of: methyl (2R)-2-amino-3-(2-chloro-4hydroxyphenyl) propanoate, D-tyrosine ethyl ester hydrochloride, methyl (2R)-2-amino-3-(2,6-dichloro-3,4-dimethoxyphenyl) propanoate H-D-Tyr(TBU)-allyl ester HCl, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy]phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy]benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyr-OMe HCl, H-3,5-diiodo-tyr-OMe HCl, H-D-3,5-diiodo-tyr-OMe HCl, H-D-tyr-OMe HCl, D-tyrosine methyl ester hydrochloride, D-tyrosine-OMe HCl, methyl D-tyrosinate hydrochloride, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr(3,5I2)-OSu, Fmoc-tyr(3—NO$_2$)—OH, and α-methyl-DL-tyrosine; and
either (i) the solid particulate material is or comprises a pharmaceutically active ingredient, (ii) said tyrosine derivative is impregnated with said solid particulate material; or (iii) the solid particulate material is or comprises a pharmaceutically active ingredient, and said tyrosine derivative is impregnated with said solid particulate material.

2. The composition of claim 1 wherein the tyrosine derivative is α-methyl-L-tyrosine.

3. The composition of claim 1 wherein the tyrosine derivative is α-methyl-D-tyrosine.

4. The composition of claim 1 wherein the solid particulate material is soluble in water.

5. The composition of claim 1 wherein the solid particulate material is not soluble in water.

6. The composition of claim 1 wherein the solid particulate material is or comprises a pharmaceutically active ingredient.

7. The composition of claim 1 wherein the pharmaceutically active ingredient has therapeutic activity in the treatment of cancer.

8. The composition of claim 1 wherein the solid particulate material is or comprises at least one of a selective estrogen receptor modulator, an aromatase inhibitor, a signal transduction inhibitor, a drug that modifies the function of proteins that regulate gene expression and other cellular functions, a drug that induces cancer cells to undergo apoptosis, and a drug that interferes with angiogenesis.

9. The composition of claim 1 wherein the pharmaceutically active ingredient is one or more of tamoxifen, toremifene, fulvestrant, anastrozole, exemestane, letrozole, imatinib mesylate, dasatinib, nilotinib, bosutinib, lapatinib, gefitinib, erlotinib, temsirolimus, everolimus, vandetanib, vemurafenib, crizotinib, vorinostat, romidepsin, bexarotene, alitretinoin, tretinoin, bortezomib, carfilzomib, pralatrexate, sorafenib, sunitinib, pazopanib, regorafenib, cabozantinib, denileukin, diftitox, ziv-aflibercept, cisplatin, cisplatinum, (cis-diamminedichloroplatinum(II)), carboplatin, oxaliplatin, benzyl isothiocyanate, acetylcholine, and dihydrotestosterone (DHT).

10. The composition of claim 1 further comprising hydrogen peroxide.

11. The composition of claim 1, wherein said tyrosine derivative is impregnated with said solid particulate material.

12. The composition of claim 1, wherein said tyrosine derivative is α-methyl-DL-tyrosine.

13. The composition of claim 1, wherein the solid particulate material is or comprises a pharmaceutically active ingredient, and said tyrosine derivative is impregnated with said solid particulate material.

* * * * *